US00PP12392P2

(12) United States Plant Patent
Zaiger et al.

(10) Patent No.: US PP12,392 P2
(45) Date of Patent: Feb. 5, 2002

(54) NECTARINE TREE NAMED: 'AUTUMN BLAZE'

(76) Inventors: Chris Floyd Zaiger, 929 Grimes Ave.; Gary Neil Zaiger, 1207 Grimes Ave.; Leith Marie Gardner, 1907 Elm Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 0 days.

(21) Appl. No.: 09/849,874

(22) Filed: May 7, 2001

(51) Int. Cl.[7] ..... A01H 5/00
(52) U.S. Cl. ..... Plt./190
(58) Field of Search ..... Plt./190

*Primary Examiner*—Bruce R. Campell
*Assistant Examiner*—Anne Marie Grünberg

(57) ABSTRACT

A new and distinct variety of nectarine tree (*Pruns* var. *nucipersica*). The following features of the tree and its fruit are characterized with the tree budded on 'Nemaguard' rootstock (non-patented), grown on Handford sandy loam soil with Storie Index rating 95 in USDA Hardiness Zone 9, near Modesto, Calif., with standard commercial fruit growing practices, such as pruning, thinning, spraying, irrigation and fertilization. Its novelty consists of the following unique combination of features that are desirable in a new variety:

1. Vigorous upright growth.
2. Regular and heavy production of fruit.
3. Late maturity of fruit.
4. Fruit with an attractive blush that partially covers a bright yellow ground color.
5. Large size of yellow flesh clingstone fruit.
6. Fruit with very good flavor and eating quality.
7. Fruit with firm flesh, good storage and shipping qualities.
8. Fruit that has the ability to remain firm on the tree 12 to 14 days after maturity, (shipping ripe).

1 Drawing Sheet

BACKGROUND OF THE VARIETY

Field of the Invention

In the field of plant genetics we conduct an extensive and continuing plant-breeding program including the origination and asexual reproduction of orchard trees, and of which interspecifics, plums, peaches, nectarines, apricots and cherries are exemplary. It is against this background of our activities that the present variety of nectarine tree was originated and asexually reproduced by us in our experimental orchard located near Modesto, Stanislaus County, California.

PRIOR VARIETIES

Among the existing varieties of nectarine and peach trees, which are known to us, and mentioned herein, are 'Zee Glo' Nectarine (U.S. Plant Pat. No. 6,408), 'O'Henry' Peach (U.S. Plant Pat. No. 2,964), 'Early Sun Grand' Nectarine (U.S. Plant Pat. No. 1,420) and 'Royal Gold' Peach (U.S. Plant Pat. No. 2,663).

ORGIN OF THE VARIETY

The present new variety of nectarine tree (*Prunus persica* var. *nucipersica*) was originated by us in our experimental orchard located near Modesto, Calif., as a first generation cross between a seedling with the field identification numbers 106ED423 an 'Zee Glo' Nectarine (U.S. Plant Pat. No. 6,408). The maternal parent (106ED423) is a third generation open pollinated seedling from a cross of 'O'Henry' Peach (U.S. Plant Pat. No. 2,964) with a seedling with the identificatin number 50G488. The paternal seedling (50G488) originated as a first generation seedling selection from 'Early Sun Grand' Nectarine (U.S. Plant Pat. No. 1,420) crossed with 'Royal Gold' Peach (U.S. Plant Pat. No. 2,663). We grew and maintained a large group of these seedlings, growing on their own root, during which time the present variety, being especially desirable for its tree and fruit characteristics described within, was selected in 1991 for asexual reproduction and commercialization.

ASEXUAL REPRODUCTION OF THE VARIETY

Asexual reproduction of the new and distinct variety of nectarine tree was by the budding to 'Nemaguard' Rootstock (non-patented), the standard rootstock for nectarines in Calif., as performed by us in our experimental orchard located near Modesto, Calif., and shows that reproductions run true to the original tree and all characteristics of the tree and its fruit are established and transmitted through succeeding asexual propagations.

SUMMARY OF THE VARIETY

The new and distinct variety of nectarine tree is of large size, vigorous, upright growth, and is a productive and regular bearer of late maturing, large size, yellow flesh, clingstone fruit with good storage and shipping qualities. The fruit is further characterized by its attractive skin color, firm flesh, very good flavor and eating quality, its ability to remain firm on the tree 12 to 14 days after maturity, (shipping ripe) and, in comparison to its pollen parent 'Zee Glo' Nectarine (U.S. Plant Pat. No. 6,408), the tree of the new variety has a higher chilling requirement, blooming 4 to 5 days later, produces fruit that has a smoother skin surface, with a shallower suture and is approximately 18 days later in maturity. In comparison to the 'Early Sun Grand' Nectarine (U.S. Plant Pat. No. 1,420), the present variety produces later maturing clingstone fruit compared to semi freestone, early maturing fruit.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a fruit divided in its suture plane to show flesh color, pit cavity and the stone remaining in place. The photographic illustration was taken shortly after being picked, (shipping ripe), and the colors are as nearly true as is reasonably possible in a color representation of this type.

DESCRIPTION OF THE VARIETY

The following is a detailed botanical description of the new variety of netarine tree, its flowers, foliage and fruit, as based on observations of 9 year old specimens grown on 'Nemaguard' Rootstock (non-patented) near Modesto, Calif., with color terminology (except those in common terms) in accordance with Reinhold Color Atlas by A. Kornerrup and J.H. Wanscher.

Tree:

*Size.*—Large. Tree height controlled by pruning to 10 to 12 feet in height and width for economical harvesting of fruit.

*Vigor.13* Vigorous. Tree growth of 5 to 7 feet in height and 4 to 5 feet in width the first growing season. Pruned during the first dormant season to 4 to 5 feet in height when primary branches are selected for desirable scaffolds and to promote proper tree growth.

*Growth.*—Upright, usually pruned to vase shape. Crotch angle approximately 35°. Heavy crop increases width of tree.

*Productivity.*—Productive, producing 1½ to several times the number of fruit for desired crop load. Fruit is thinned and spaced to the desired number to develop marketable size fruit. Number of fruit set varies with climatic conditions at bloom time.

*Bearer.*—Regular, has produced adequate fruit set for 8 consecutive years. No alternate bearing observed.

*Form.*—Pruned to vase shape.

*Density.*—Medium dense, usually pruned to vase shape by removing small limbs from center of tree to allow for more sunlight and air movement, which enhances fruit color and Brix.

*Hardiness.*—Tree grown in USDA Hardiness Zone 9, winter chilling requirement is approximately 800 hours below 45° F. Hardy in all stone fruit growing areas of California.

*Fertility.*—Self-fertile.

Trunk:

*Size.*—Medium to large. Average circumference of 19 inches at 14 inches above ground on a 9 year old tree.

*Surface texture.*—Medium shaggy. Roughness increases with age of tree.

*Color.*—Brown to soot brown (5-F-3) to (5-F-5).

Branches:

*Size.*—Medium. Circumference averages 8¼ inches at 52 inches above ground.

*Surface texture.*—Smooth on new growth to medium rough on old growth. Roughness increases with age of branches.

*Lenticels.*—Number — medium. Average number of 26 in a 4 square inch surface. Small to medium in size, average length 3/32 inch, average width 3/64 inch. Size increases as branches become larger. Color — light brown to yellowish brown (5-D-8) to (5-E-8).

*Color.*—First years new growth varies from pea green to yellowish green (29-D-7) to (29-D-8). Mature growth varies from light brown to yellowish brown (5-D-8) to (5-E-8). Color becomes darker with age of growth.

Leaves:

*Size.*—Large. Average length 5 9/16 inches. Average width 1½ inches.

*Form.*—Lanceolate.

*Apex.*—Acuminate.

*Base.*—Cuneate.

*Margin.*—Serrate.

*Thickness.*—Medium.

*Surface texture.*—Upper surface relatively smooth, slight indentations over leaf veins, glabrous. Lower surface relatively smooth, small ridges created by midrib and pinnate venation, glabrous.

*Petiole.13* Medium. Average length 39/64 inch. Average width 3/64 inch. Grooved longitudinally. Color varies from green to yellowish green (29-D-7) to (29-D-8).

*Glands.*—Reniform. Small to medium in size, average diameter 1/32 inch. Number varies from 1 to 4. Average number 2. Color — grayish green to green (29-C-7) to (29-C-8). Sticky gland secretion collects dust and impurities, which create a darker color. Location on the base of the leaf blade and upper portion of the petiole.

*Color.*—Upper surface-green to dark green (28-F-6) to 28-F-8). Lower surface— light green to green (28-E-6) to (28-E-8).

Flower buds:

*Size.*—Medium to large. Average length 19/32 inch. Average diameter 13/32 inch, 3 days before bloom.

*Form.*—Plump, conical, becomes elongated before opening.

*Color.*—Pink to pastel pink (12-A3) to (12-A-4).

*Hardiness.*—Hardy in all stone fruit growing areas of California.

Flowers:

*Size.*—Large, showy. Average height 25/32 inch. Average diameter 1 15/16 inches.

*Petal.*—Shape — orbicular, alternately positioned to sepals. Narrows at point of attachment. Surface edge varies from smooth to scalloped. Average length 15/16 inch. Average width 13/16 inch. Color — pink to pastel pink (12-A-3) to (12-A-4).

*Sepals.*—Number five. Alternately arranged with petals. Average length 21/64 inch. Average width 7/32 inch at point of attachment. Color — upper surface grayish yellow to olive yellow (3-C-7) to (3-D-7), glabrous. Lower surface red to brownish red (10-C-6) to (10-D-6), pubescent. Fades with age of flower.

*Stamens.*—Number of stamens varies from 43 to 46, average number 44. Average length 33/64 inch. Filament color — white (1-A-1), turning pink with age of bloom. Anther color — cerise red (12-C-8).

*Pollen.*—Present, self-fertile. Color — light yellow to yellow (4-A-3) to (4-A-5).

*Pistil.*—Usually one, varies from 1 to 2. Average length 23/32 inch. Color — yellow white to pastel yellow (1-A-2) to (1-A-4). Stigma slightly below anthers. No pubescence.

*Aroma.*—Slight, sweet fragrance.

*Pedicel.*—Average length 3/16 inch. Average width 3/32 inch. Color — olive yellow (3-C-6).

*Blooming period.*—Date of First Bloom Mar. 4, 1999. Date of Petal Fall Mar. 13, 1999. Varies slightly with climatic conditions.

*Color.*—Pink to pastel pink (12-A-3) to (12-A-4), color fades with age of bloom.

Fruit:

*Maturity when described.*—Shipping ripe.

*Date of First picking.*—Aug. 23, 1999.

*Date of last picking.*—Aug. 28, 1999. Varies slightly with climatic conditions.

*Size.*—Average diameter axially 2⅝ inches to 2 55/64 inches. Average transversely in suture plane 2 9/16 inches to 2 21/32 inches. Average weight 177 grams, varies from 170 to 186 grams. Average weight varies slightly with fertility of the soil, amount of thinning and climatic conditions.

*Form.*—Nearly globose, only slightly elongated.

*Suture.*—Shallow, extends from base to apex.

*Ventral surface.*—Usually rounded, some fruit slightly lipped.

*Apex.*—Usually rounded, varies from slight tip to slightly retuse.

*Base.*—Retuse.

*Cavity.*—Rounded to slightly elongated in suture plane. Average depth — 7/16 inch. Average breadth — ¾ inch.

Flesh:

*Ripens.*—Evenly.

*Texture.*—Firm, meaty.

*Fibers.*—Few, small and tender.

*Aroma.*—Slight.

*Amydgalin.*—Undetected.

*Eating quality.*—Very good.

*Flavor.*—Very good.

*Juice.*—Moderate amount, good balance between the acid and sugar.

*Brix.*—Average Brix 17.0°, varies slightly with number of fruit per tree and climatic conditions.

*Color.*—Yellow to vivid yellow (3-A-6) to (3-A-8). Pit cavity varies from deep red to Turkish red (10-C-8) to (10-D-8). Slight bleeding of red from pit cavity into flesh.

Stem:

*Size.*—Average length 7/16 inch, enlarged at point of fruit attachment. Average diameter ⅛ inch.

*Color.*—Grayish green to apple green (29-C-6) to (29-C-7).

Skin:

*Thickness.*—Medium, normal compared to most commercial varieties of nectarines, shows no excessive scarring in picking and packing trials.

*Texture.*—Medium, tenacious to the flesh.

*Astringency.*—None.

*Bloom.*—Wanting.

*Tendency to crack.*—None.

*Color.13* Light yellow to orange yellow (3-A8) to (4-A-7), ground color. Red to lake red blush (9-C-7) to (9-C-8) covering most of the surface. Areas of ground color create an attractive mottled pattern to the fruit.

Stone:

*Type.*—Clingstone.

*Size.*—Large. Average length 1 15/32 inches. Average width 1 1/16 inch. Average thickness 11/16 inch.

*Form.*—Varies from ovoid to obovoid.

*Base.*—Usually straight, varies from straight to rounded.

*Apex.*—Cuspidate, very short.

*Surface.*—Irregularly furrowed toward apex, pitted toward base, pit cavities vary from rounded to elongated. One long groove on each side of suture. Ridges relatively wide with rough surface.

*Sides.*—Equal to unequal. Some stones have one side slightly larger, extending farther from the suture plane.

*Tendency to split.*—None.

*Color.*—Violet brown (11-E-5) to (11-F-5), when dry.

Kernel: Average length 49/64 inch. Average width 31/64 inch.

*Seed coat color.*—grayish orange to apricot yellow (5-B-4) to (5-B-6).

*Taste.*—bitter.

*Amygdalin.*—Abundant.

Use: Dessert. Market — local and long distance.

Keeping quality: Excellent, fruit holds firm for three weeks at 38 to 42° F. in cold storage with no internal breakdown of flesh or appreciable loss of eating quality.

Shipping quality: Good, picking and packing of fruit gave minimal bruising or scarring of flesh or skin.

Disease resistance susceptibilty: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety of selection observed during indexing of plant characteristics with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of nectarine tree, substantially as illustrated and described, characterized by its large size, vigorous, upright growth, and being a productive and regular bearer of large, yellow flesh, clingstone fruit with an attractive skin color, the fruit is further characterized by having very good flavor and eating quality, flesh that has the ability to remain firm on the tree 12 to 14 days after maturity and, in comparison to its pollen parent 'Zee Glo' Nectarine (U.S. Plant Pat. No. 6,408), the new variety is approximately 18 days later in maturity.

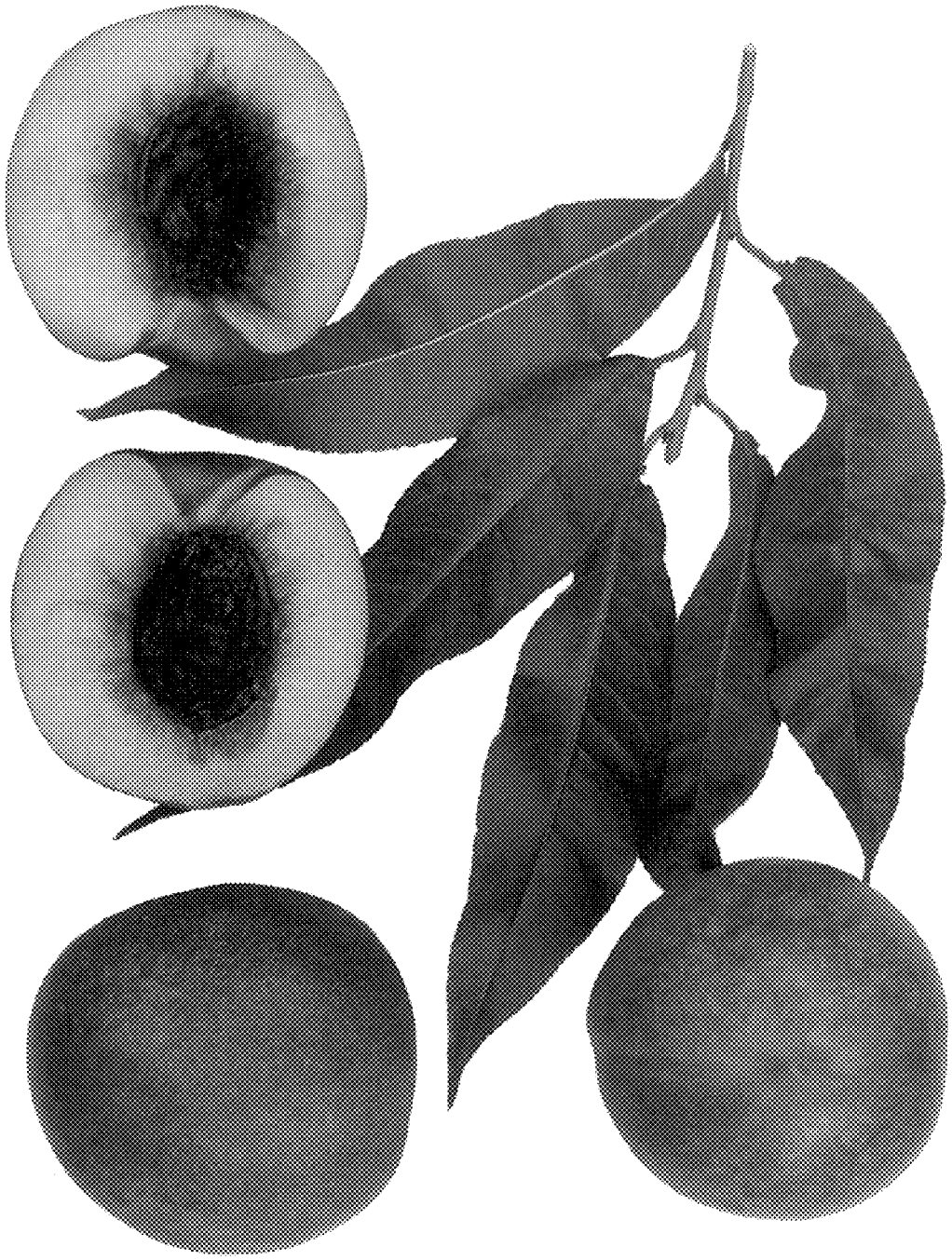

* * * * *